United States Patent [19] [11] Patent Number: 4,590,795
Oetiker et al. [45] Date of Patent: May 27, 1986

[54] PROCESS AND DEVICE FOR CONTINUOUSLY DETERMINING THE MOISTURE CONTENT OF SPOILABLE FOODSTUFFS

[75] Inventors: Hans Oetiker, St. Gallen; Emanuel Kummer, Gossau, both of Switzerland

[73] Assignee: Gerbruder Buhler AG, Switzerland

[21] Appl. No.: 557,612

[22] Filed: Dec. 2, 1983

Related U.S. Application Data

[60] Division of Ser. No. 392,137, Jun. 25, 1982, which is a continuation-in-part of Ser. No. 355,596, Feb. 17, 1982.

[30] Foreign Application Priority Data

Jun. 30, 1981 [EP]  European Pat. Off. ........ 81105064.0

[51] Int. Cl.[4] ........................................... G01N 27/22
[52] U.S. Cl. ..................... 73/73; 73/304 C; 222/57
[58] Field of Search ........... 73/863.51, 863.73, 290 R, 73/304 C, 73; 324/61 R; 222/57

[56] References Cited

U.S. PATENT DOCUMENTS

| | | | |
|---|---|---|---|
| 1,569,201 | 1/1926 | Piersall | 222/57 |
| 2,120,437 | 6/1938 | Feese | 222/57 |
| 2,665,409 | 1/1954 | Rogers | 73/863.51 |
| 2,670,629 | 3/1954 | Belden | 73/863.51 |
| 3,290,938 | 12/1966 | Miller | 73/290 R |
| 3,353,713 | 11/1967 | Scott | 222/57 |
| 3,401,562 | 9/1968 | Reaney | 73/290 R |
| 3,994,169 | 11/1976 | Wolford | 73/290 R |
| 4,133,454 | 1/1979 | Arthur | 73/304 C |
| 4,168,466 | 9/1979 | Boldt | 324/61 R |
| 4,354,622 | 10/1982 | Wood | 73/863.73 |

Primary Examiner—Charles Frankfort
Assistant Examiner—Denis E. Corr
Attorney, Agent, or Firm—Darby & Darby

[57] ABSTRACT

A process and apparatus are disclosed for continuously determining the moisture content of a spoilable foodstuff, in particular, of grain and processed products of the latter, which is moved along a production line as a product stream and passed, at least in part, through a measuring section of a housing in accordance with the process, a pourable average of the product stream is created continuously within the measuring section, and the product moisture content of this product average is measured electrically on a continuous basis. In accordance with the device, the measuring housing has a capacitor as a continuous-flow measuring section and a device for continuously controlling the creation of a pourable product average. One of the central concepts of the invention is found in the interaction of the following factors: —continuous creation of a product average, continuous trickling-type flow of the product, with simultaneous electrical measurement on a continuous basis.

20 Claims, 7 Drawing Figures

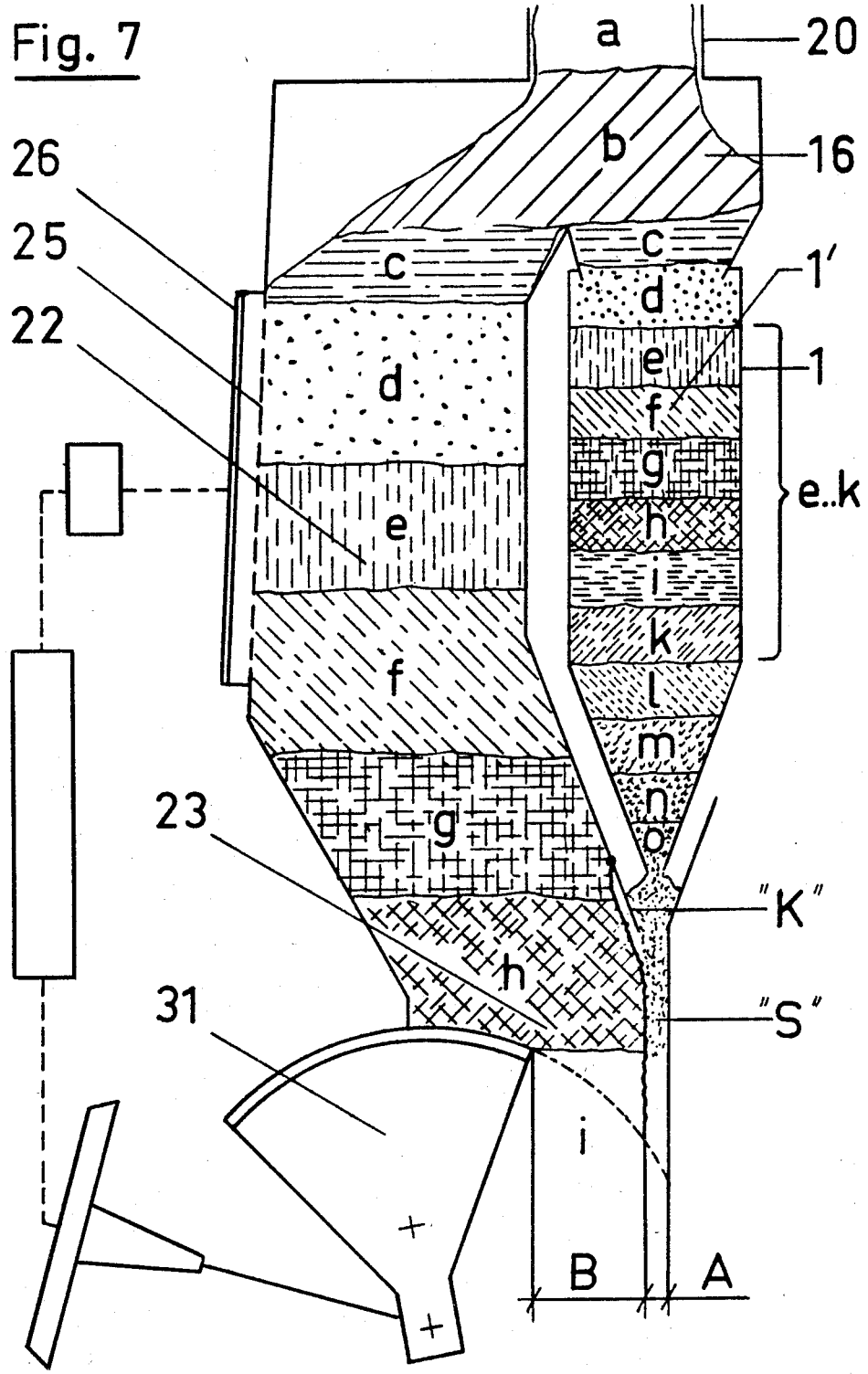

PROCESS AND DEVICE FOR CONTINUOUSLY DETERMINING THE MOISTURE CONTENT OF SPOILABLE FOODSTUFFS

This is a division of application Ser. No. 392,137, filed June 25, 1982 which is a continuation-in-part of U.S. patent application Ser. No. 355,595, filed Feb. 17, 1982, which resulted from International Application No. PCT/CH80/00150 filed Dec. 5, 1980.

BACKGROUND OF THE INVENTION

The invention concerns a process for continuously determining the moisture content of a spoilable foodstuff, in particular, of grain and processed products of the latter (referred to as "product"), which is moved along a production line as a product stream and passed, at least in part, through a measuring section.

The invention also concerns a device, especially for carrying out the invention process, for continuously determining the moisture content of spoilable foodstuffs, in particular, grain and processed products of the latter, as it is moved through a measuring housing.

In a milling operation, to the present various material characteristics, and in particular moisture content, can only be measured with unsatisfactory precision.

The causes for this lie in a large number of factors. The good itself is to be found in two extreme conditions, namely on the one hand at rest, stored in silos, and on the other hand in flow from processing stage to processing stage. It is particularly difficult to obtain exact material values in a continually moving product, and therefore in practice, the laboratory method performed on samples has been used for determination of the exact value. To determine exact material values of a large quantity of a pourable good regularly entails the testing of many samples and the statistical evaluation of the result. Manipulation of the sample taking mechanism is awkward, particularly for large silo cells, since to the extent possible, samples must be drawn from varous places within the silo, while within silos very high pressures and compressions are usual.

A further difficulty lies in the fact that the product moisture can vary between relatively wide extreme values, which has a direct influence on the product dry volume, and also, for example, the density and electrical conductivity.

In the mill, generally various grain types are mixed together. However, it is not necessary that the mixing of the various sorts be performed very precisely, since in the subsequent processing stages a repeated mixing of the individual fractions can be performed if required. The individual type fractions have various physical properties among them, and in particular the bulk weight is different, and usually the product moisture content as well.

Constrained by these problematics, the measurement by sampling of individual physical quantities has remained an unsolved problem, and this applies quite particularly to the exact determination of the water content in the product.

In a familiar process for determination of the water content in grain, the grain is removed by a mechanism from a product stream in a batch or quasi-continuous operation, and poured in a certain weighed quantity into a measurement container. The measurement container is in part constituted as a condenser, and a measurement is made by determination of an electrical value in the form of the capacitance of the condenser constituted by the container with the product, and in evaluation is converted to the quantity of water present in the sample. This instrument reflects the actual water content of the measurement sample, but it is questionable with this method, whether the measurement values are representative of the entire product stream.

If the product is to be moistened to a particular water content, the product throughput must be received in a subsequent continuously operating weighing system, and the necessary supplemental water quantity computed and added. Although this system is employed relatively frequently in practice, it may often be insufficient for the requirements in a mill. If the moistures or water contents produced are namely determined by an exact laboratory method, for example, in a drying oven, variations in the relative moisture content of frequently up to half a percent, and sometimes up to one percent are discovered. The electrical measurement method here described has the particular failing that the values determined are very much type dependent. To exclude this factor, calibration must be performed for each grain type before beginning measurement. For transparent reasons, this calibration is useless in the case of a mixing of more than one type, if the mixing ratio itself is not precisely known or precisely defined.

Appearing especially critical is the question of the water content, with regard to whether the water content has changed soon or long before the measurement. The electrical conductivity is affected by each of the parameters cited.

In milling to the present, in the majority, only the tradiational laboratory measurement methods have been given confidence, which, however, has limited a further automation of mills, since such decisive parameters as the exact throughput quantity, the exact moisture content, or even the exact level of the good could not be monitored with sufficient confidence.

Other measuring processes have not found any substantive application in the milling filed. Measuring processes with microwaves, gamma-rays and the like are not being considered due to the risks inherent in the rays. Other measuring processes on the other hand are suitable for dead materials, textiles, paper, sand and the like and are precluded from grain which is a living substance, since the measuring results are totally unusable.

A part of the invention is to overcome the known deficiency in the state of the art, in particular to find a new process for determination of physical quantities, in which the values determined for as large as possible a quantity of product and to as high as possible a precision are made available. The process should render unnecessary any constant recalibration both with respect to special grain types, and with respect to short and long term behavior. The solution is to be simple and economical to manufacture, and be operable even by personnel with little training.

In relation to the process, the solution provided by the invention is distinguished by the fact that a pourable average of the product stream is created continuously within the measuring section, and the product moisture content of this product average is measured electrically on a continuous basis.

In relation to the device, the solution provided by the invention is distinguished by the fact that the measuring housing has a capacitor as a continuous-flow measuring section and a device for continuously controlling the creation of a pourable product average.

It has been shown that the new solution concept has resulted in a substantial step forward in terms of increasing operational reliability. The new invention establishes a new branch for automation of mill operation. On one hand, the new process permits the moisture content of the product to be determined with considerably higher accuracy, and on the other, it makes possible the elimination of moisture as a source of problems, for example, in the exact measurement of flow rates or levels.

One of the central concepts of the invention is found in the interaction of the following factors:
  continuous creation of a product average
  continuous trickling-type flow of the product
  with simultaneous electrical measurement on a continuous basis The invention suggests first of all that a product average be produced in place of the awkward process employed to date of taking samples and evaluating them individually. In this procss the product average should be constantly reformed in a continuous, trickling flow with simultaneous electrical measurement of the product.

The quantity of product measured may actually lie within a range from a few percent of the entire quantity of product up to 100 percent, according to the particular situation. In the case of the known process, the fact has been disregarded that the shape and the composition of the measurement sample are just as important as the measuring process itself. With poor sampling, even the best measuring method is rendered unusable. Practice has shown that measurement values obtained according to the principles of the invention even lie within the mean error of the best laboratory methods; moisture content is therefore obviously determined more effectively than in all methods previously used. Moreover, the invention also makes possible a large number of particularly advantageous design elaborations. Thus, according to the invention a relatively large quantity of product, for example, five to ten liters, may be determined with a single measuring process.

It is preferable for an average of the product stream to be produced in the measuring section with respect to time, such that a constant percentage of the product stream is scanned for the determination of moisture content. To extend this concept, this percentage may also be present. In this manner, as mentioned in the beginning, it is possible with unknown mistures to measure a substantially larger proportion of the product, and therefore for the measuring reliability to be increased.

Until today it has not been possible to explain with certainty the influence of individual factors, in particular, the reciprocal influence of the latter.

It is also of particular importance that the movement of the product be retarded in the measuring section in a manner that is free of pressure, that is, occurring by means of gravity alone; that it trickle, as it were, through the measuring section as in an egg timer or hourglass; and that the moisture content be measured during this process.

It is preferable for a first partial flow of product to be passed through the measuring section and a second partial flow through a bypass, each by gravitational force, and to be retarded simultaneously in their downward movement in the section of a measuring housing formed by the measuring section and the bypass, in particular, to be delayed to different degrees in the measuring section and the bypass. It is advisable for the two partial flows to be created on the overflow principle and to be reunited beneath the measuring section in such a manner that a controlled backlog in the measuring section is created in the area where the two partial flows are brought together. The outlet port from the measuring section can be designed as a presetable gate valve in order to bring about the passage of a certain desired percentage of the product through the measuring section. The movement of the product in the bypass is controlled according to another idea, for the purpose of maintaining a constant level in the bypass to ensure a constant product backlog in the measuring section.

The capacitance in the measuring section designed as a measuring capacitor is preferably measured directly, and the values obtained delivered to an electronic evaluator for the determination of the moisture content of the product. It is preferable for the measurement capacitor to be charged to a certain voltage in a first phase, and in a second phase for a reference capacitor to be connected to the measuring capacitor, the measuring capacitor to be discharged into the reference capacitor, and the voltage obtained in this manner to be measured over the reference capacitor and delivered to the electronic evaluator, the two phases being repeated in a cyclical manner, the reference capacitor being discharged during the first phase and the voltage across the reference capacitor being delivered to a reservoir at the end of the second phase. In the reservoir a mean value may also be formed from several measured values for determining the moisture content of the product. Another possible elaboration is for the product to be weighted in the measuring section and and the instantaneous weight value to be determined during the electrical measurement, the product stream in the measuring section being controlled in such a manner that the measuring section remains essentially full at all times.

Problems encountered with extreme product mixtures may be avoided with the simultaneous determination of the product moisture content and the weight of the content of the measuring section. Practice has already established that the invention constitutes a considerable developmental advancement, by virtue of the fact that the two partial streams are reunited forming an enclosed product column, and the product movement is regulated to a constant level in the bypass duct, and since the instantaneous flow rate is determined immediately afterward in a continuous process.

One of the secrets of determining exactly the instantaneous throughput of a product stream, for example, by means of appropriately designed deflection plates, is holding the feed relations constant to the extent possible. It has been found that the solution according to the invention produces ideal conditions for quantitative measurement with deflection plates. With the formation of an enclosed product column, disturbances from spurious air currents, etc., are eliminated very effectively and free of charge.

Using the determined moisture content of the product and the instantaneous flow rate, the amount of water lacking—relative to a desired moisture content value—may be determined to the same degree of accuracy in a computer, and a subsequent device for moistening the product may be immediately adjusted.

At any point in time, a product average is being created. The moisture content of this product average is measured on a continuous basis. The measurement produces a true value by which the addition of water may be controlled directly, as a result of the comparison of desired value and actual value. No oscillation buildup occurs, since a basic problem factor, product inhomogeneity, is eliminated by the averaging process. At the same time, full advantage may be taken of the benefits of the electronic measurement method, which also permits averaging, and it may e practically employed for automatically regulating the wetting of grain. The simultaneity of all the processes in the system gives it an unanticipated precision and reliability, to a degree that far surpasses past practice. All the advantages of forward control (regulation) therefore take effect.

To bring about movement of the product by the effect of gravity alone, the product supply ducts in the measurement housing run essentially in a vertical direction.

It is preferable for the device used to continuously control the product average to have a level-regulating mechanism. A bypass is assigned to the measuring section to divert a portion of the product stream, as well as a regulating mechanism for the purpose of adjusting the product in the by-ass to a constant level and the product in the measuring section to bring about continuous averaging. Simple construction is achieved by placing the measuring section and the bypass immediately adjacent to each other and connecting them by means of an overflow duct and a common product outlet, and also by the fact that the product inlet of the measuring chamber discharges essentially directly above the measuring section, and the product may be guided, flowing freely, through the overflow duct into the bypass. To retard the product it is also advisable for the invention device to have a throughput-regulating mechanism at the product outlet that is controlled by a level sensor located in the regulating duct, or bypass. The level sensor is preferably executed as a membrane located on the side of the regulating duct, which is preferably connected by pneumatic actuating elements to the overflow-regulating mechanism. Manual actuators are also provided for opening and closing the throughput-regulating mechanism, so that the entire device may be emptied when required.

In its preferred and most frequent application, the invention device is provided with a throughput measuring mechanism, which determines its instantaneous throughput for the purpose of computing the amount of water to be added.

It is also possible to install the invention device directly beneath a storage container, such that the delivery output of the storage container may be regulated by the invention device itself. For this purpose it is preferable for the device to have a throughput regulating loop, with a flow rate regulating mechanism and a throughput measuring instrument, in which the electronic evaluator serves as a comparator for comparing the actual value, supplied by the throughput measuring instrument, to the desired value, supplied by a corresponding desired value control unit, and adjusts the flow rate regulating mechanism to maintain the desired value. The two last-named applications make possible ideal conditions for continuously measuring the flow rate of the product. In both cases the continuous flow rate measuring device receives a constant stream of product without spurious air disruptions, as a result of the enclosed product column created by the backlog.

As a result of the combination of the measurement of moisture content according to the invention and the immediately following continuous measurement of product quantity, a subsequent device for wetting or drying the grain can be controlled reliably and very accurately by an electronic evaluator and a second computer, which has not been possible previously in practice. Another possible elaboration is to design the capacitor arrangement as a balance receptacle, or to support it on pressure pickups, so that the balance signal can be processed to determine the settled apparent density of the product within the measuring section.

A further idea for constructional elaboration is for the measuring section to be designed within a measuring chamber in the measurement housing. For this purpose a vertical section of the outer wall of the measuring chamber is designed as a first capacitor plate, and a second capacitor plate is located inside the measuring chamber.

The invention will now be explained in further detail by means of several exemplary executions.

BRIEF DESCRIPTION OF THE DRAWINGS

FIG. 7 is a schematic representation of averaging in measuring chamber.

DESCRIPTION OF THE PREFERRED EMBODIMENTS

Figure 1:
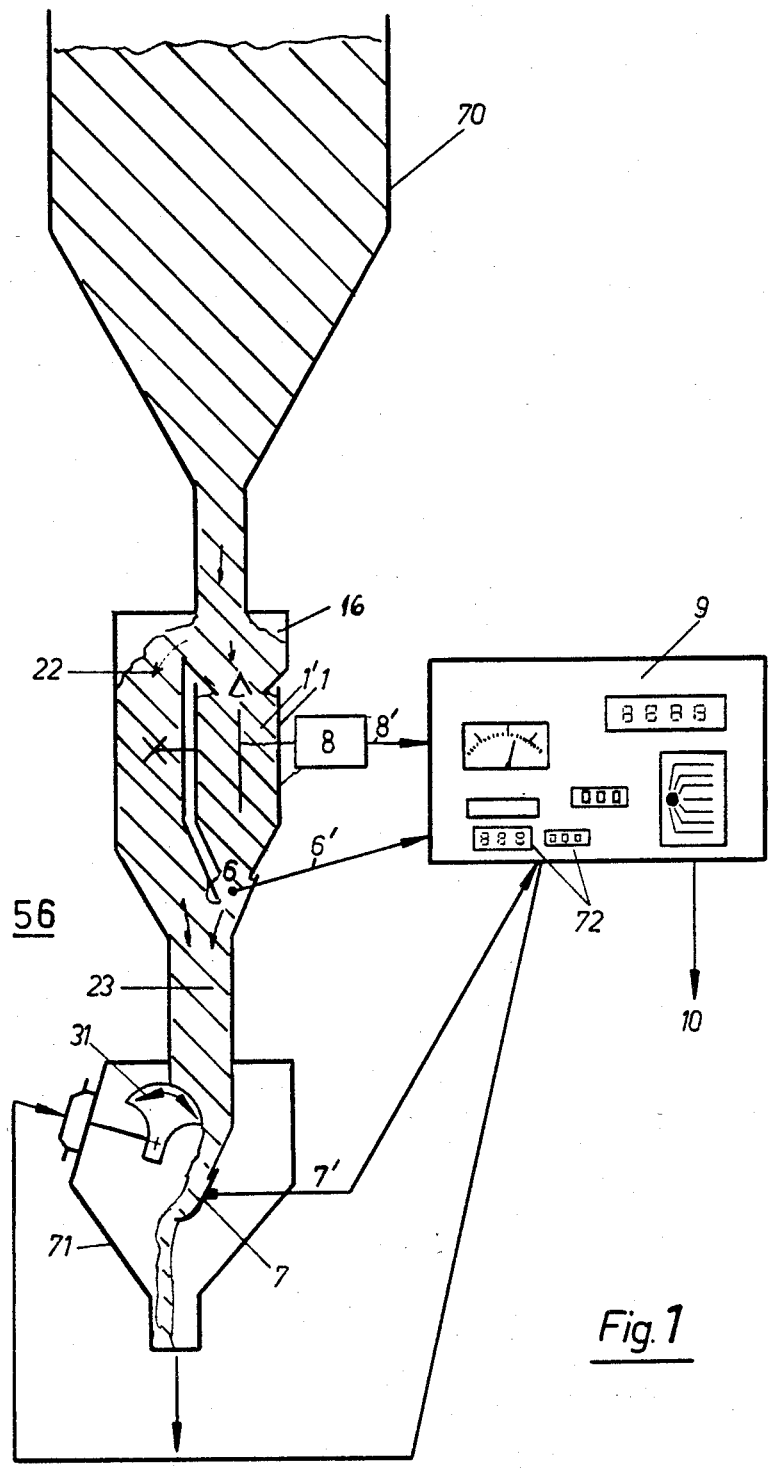
FIG. 1 shows a measurement of moisture content and control of flow rate through a measuring section; directly under a silo.

FIG. 1 shows a principle representation of a device 56 positioned beneath a compartment 70 of a silo for continuously determining the moisture content of grain, in which the movement of the grain occurs essentially as a result of gravitational force and the shape of device 56 alone. Device 56 exhibits a measuring housing 16 adjacent to the outlet of silo compartment 70 that tapers at its downstream end to a product outlet 23. Following product outlet 23 downstream is a throughput control loop 71. The measurement housing 17 is designed and constructed in such a way that the longitudinal axes of the regulating duct 22 and the measuring chamber 1 run essentially vertically, or in the direction of the earth's gravitational field, and the bulk material trickles through them, as it were, in a manner similar to that of sand in an hourglass. The measuring chamber 1 has a bulk material measuring duct, or measuring section 1', that is designed as a capacitor for capacitively measuring the moisture content of the grain. As illustrated on an enlarged scale in FIG. 6, an inner wall of the measuring chamber 1 is designed as a first capacitor plate 4, and a second capacitor plate 5 is positioned inside the chamber. Under the measuring chamber 1 is a bulk material temperature sensor 6. Beneath the product outlet 23 is a throughput measuring device 7. The measured values are converted partly in a converter 8 and an electronic evaluator 9 into the desired parameter. The initial values of bulk material temperature sensor 6, throughput measuring device 7, and a converter 8 are delivered by signal conductor 6', 7', or 8' to the electronic evaluator 9.

The solution illustrated in FIG. 1 is in principle the basis for measuring the moisture content of grain and may be employed-supplemented with the above-mentioned througput measuring device 7 and a (second) computer 10 (see FIG. 6)—directly for controlling wetting, that is, for influencing the moisture content of the grain in the direction of a certain value.

Figure 2:
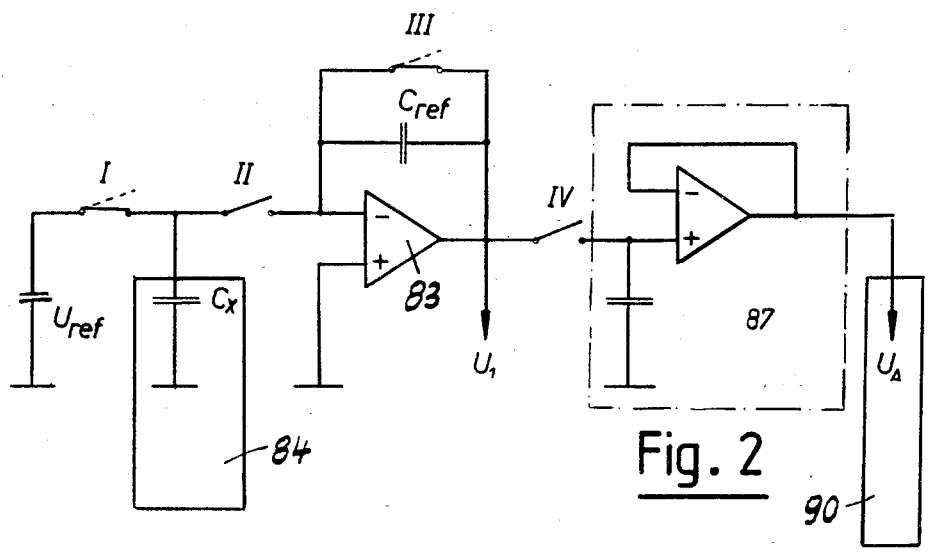
FIG. 2 is a diagrammatic representation of electrical measuring process.

In FIG. 2 is a conceptual representation of the new measurement process. In a measurement container 84 configured as a condenser, analogous to the measurement container 1 of FIG. 1, the capacitance is measured. For the description of the performance of the measurement, reference will be made at the same time to FIGS. 3 and 4 as well.

Figure 3:
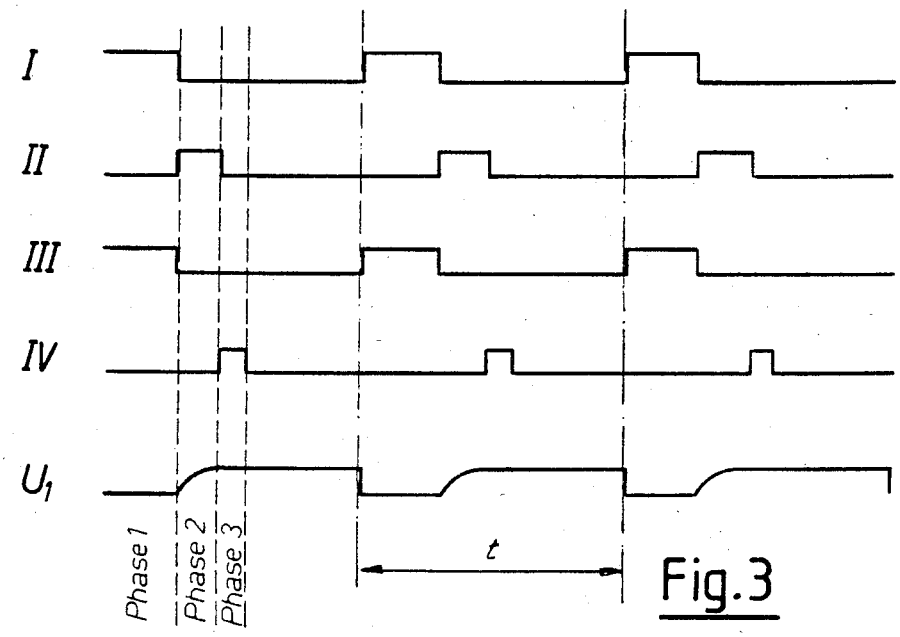
FIG. 3 shows positioning of individual switches in temporal course according to FIG. 2.

FIG. 3 shows the individual switch positions of the switches I-IV in FIG. 2 during the measurement, and the trace of the voltage $U_1$.

In an initial phase, the measurement condenser $C_x$ is charged to a particular voltage $U_{ref}$. At the same time, the reference condenser $C_{ref}$ is discharged. Switches I and III are closed. Switches II and IV are opened (position as in FIG. 2). The voltages U' is still zero in the initial phase. In the second phase, the charge of the measurement condenser $C_x$ is transferred to the reference condenser $C_{ref}$. The switch II is closed for this purpose, and the switches I, III and IV are opened. The voltage U' rises until the measurement condenser is fully discharged. This charge transfer is effected by means of the operational amplifier 83. In a third phase, the voltage of U+ is transferred to an analog memory 87. For this purpose, the switch IV is closed, and the switches I-III opened. This phased charging and discharging of the measurement and reference condensers $C_x$ and $C_{ref}$ is controlled by preference by the cycle of the power supply frequency.

Figure 4:
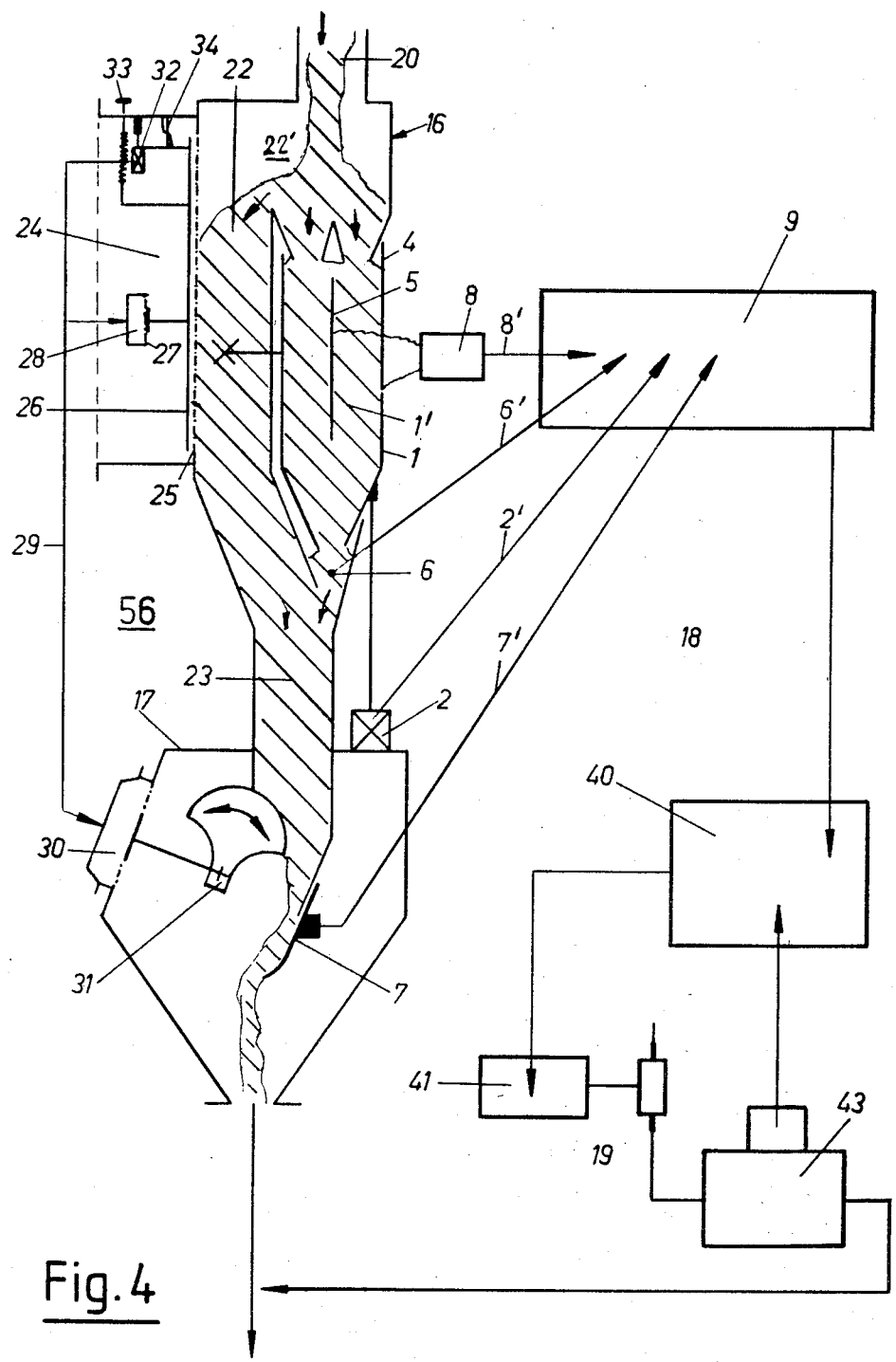
FIG. 4 is a principal diagram for control and regulation of a grain wetting device.

In FIG. 4 is represented an application of the invention for measurement and control of the water content of a pourable goods. The apparatus displays a measurement container 1 with a throughput regulating mechanism 17, and a regulation and control loop 18, which includes an evaluation circuit 9 and a wetting apparatus 19.

The measurement section 16 has an inlet 20, opening essentially vertically above the measurement container 1. Parallel to the measurement container 1 runs a regulating channel 22. The regulating channel 22 and the measurement contain 1 flow together in the region above the product outlet 23. The product outlet 23 is controlled by means of a throughput regulating mechanism 17, in which a level detector 24 is included in the form of a membrane 25 in the side of the regulating channel 22.

A strut 26 is pivoted on a joint 34, and a pneumatic regulator valve 32 is connected with the strut 26. At a certain pressure of the product, through the membrane 25 and the strut 26, the pneumatic regulator valve 32 is actuated, producing an air pressure in a duct 29. This air pressure operates a pressure cylinder 30, which in turn controls the gate 31 at the product outlet 23. The same pressure present in the duct 29 also enters a pressure chamber 28 and acts on a membrane 27. Here the pressure serves as a compensating pressure against the product pressure.

In the regulating channel 22 are also manual actuating means for the opening and closing of the throughput regulating mechanism 17. A screw 33 and the strut 26 permit actuation of the pneumatic regulator valve 32, and thus completely open or close the gate 31. With this manual actuation mechanism, it is possible to fully empty the pourable good measurement section 1, for example to perform testing of the measurement condenser.

Below the product outlet 23 of the measurement container 1 is placed a throughput quantity measurement instrument 7, which establishes the instantaneous throughput quantity. Thus with the measurement values of the condenser, of the pourable goods temperature sensor 6, the scale 2 and the throughput quantity measurement instrument 7, a moisture deficiency value can be determined. In the evaluation circuit 9, the moisture deficiency value is passed as a control quantity to a regulator 40, which controls a motor 41 which conveys the computed quantity of water lacking into the product stream. As a control, the water quantity delivered is echoed by a check post 43.

Figure 5:
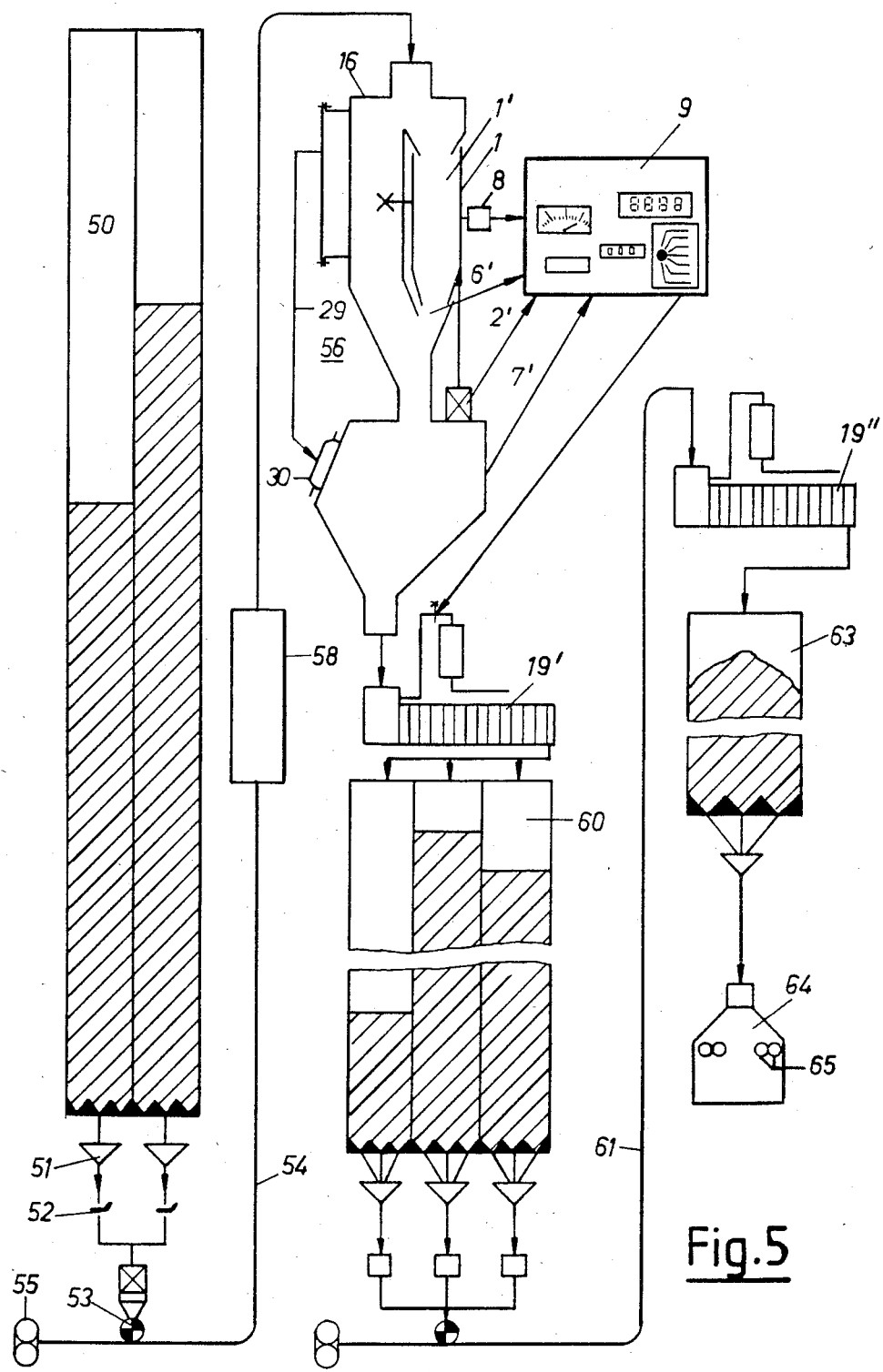
FIG. 5 shows an application of solntion shown in FIG. 4 in a mill or a cleaning room.

In FIG. 5, the components are the same as those in FIG. 4 and are given the same reference numbers. FIG. 5 shows the basic plan of an installation with the new measurement apparatus.

The raw product is drawn from storage bins 50 through special outlets 51, which hinder separation, an approximate outlet rate is established by means of a gate 52, and is fed through a bucket wheel sluice 53 and a pneumatic barrow train 54 supplied with air from the blower 55, into the moisture measurement apparatus 56.

The details of construction of the measurement container 1 are represented in FIG. 4. The wetting apparatus 19' in the preferred solution has a closed housing with a rapidly turning intensive wetting rotor. The water content of the grain is determined in the measurement container 1, and regulated in an open or direct control loop by means of the evaluation circuit 9 and the wetting apparatus 19'.

The wetted grain is conveyed into standing bins 60. Depending on the wheat variety and the desired flour products, the grain can be removed from the standing bins 60 after an appropriate number of hours, to be conveyed through another pneumatic transport 61 into an intensive setting apparatus 19'', where a small additional quantity of water is added. Usually here a few tenths of a percent of water is applied as a water film on the grain, and after a working period in standing bins 63, the grain is transferred directly to the rolling carriages 64.

Figure 6:
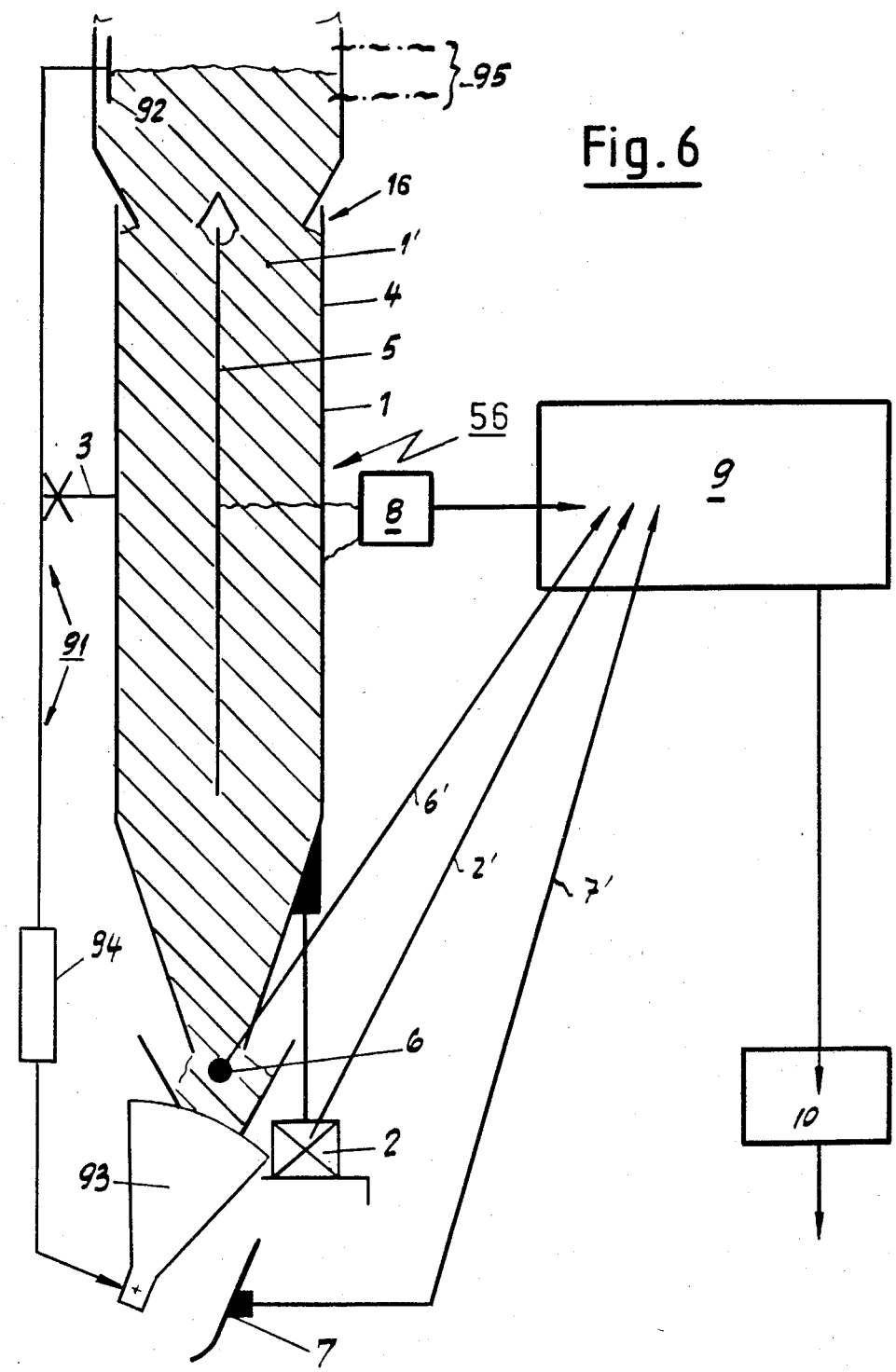
FIG. 6 shows a measurement of moisture content and throughput directly in product.

FIG. 6 shows a particularly advantageous example of realization built on the basic elements of FIGS. 1, 2 and 3. The corresponding parts are therefore labelled with the same reference numbers. In FIG. 6, there is in addition a control mechanism 91 to control the sinking movement of the good in the measurement section 1' or in the measurement container 1 forming part of the measurement housing 16. The control mechanism 91 includes a level sensor 92 and an adjusting gate 93. The signals from the level sensor 92 are processed by a control unit 94.

The purpose of the control mechanism 91 is for the product to be passed with retardation through the measurement section 1' or the measurement container 1. The solution in FIG. 6 can be employed in such a way that the entire *oods stream is passed through the measurement section 1'. The total throughput quantity through the measurement section need not be changed in this application. The control mechanism 91 serves merely to impede the product movemenl to a greater or lesser extent, so that the measurement container 1 is constantly filled with the goods. To ensure filling, by means of the control mechanism 91, through regulation of the opening of the adjusting gate 93, the level of the goods is maintained within a constanl range 95.

Through means not represented, it can be ensured that the extreme positions without product and without further feed of product, or the closed position of the adjusting gate 93 resulting in possible false indications or false commands from the evaluation circuitry are avoided.

FIG. 6 shows the further possibility of the determination of the weight of the goods by a weighing mechanism, consisting of a pressure sensor or scale 2 and a corresponding support pivot 3. In this example, the measurement container 1 is simultaneously configured as a weighing container. The weighing container can be used as a continuous throughput scale, or as a batch scale, depending on the position of the adjusting gate 93.

It has been found that in the case of extreme product variations, particularly with regard to electrical conductivity, the additional weighing, and evaluation of the weight measurement, advantageously determined simultaneously with the electrical measurement, yields an increased level of confidence for correction of the measurement value.

FIG. 7 shows in somewhat enlarged scale the continuous averaging of the product in the measuring section 1' within measuring chamber 1 shown in FIG. 1 and FIG. 4.

This continuous averaging, that is, continuous formation of a constantly representative cross section of the bulk material flowing through intake 20, undergoes constant self-adjustment in the invention device 56.

It is assumed in the following that the composition of the product, that is, the individual components of the product, vary over time. For the purpose of illustration a charge-type or batch-type variation is represented. The influence of the averaging, however, may be achieved in exactly the same manner if this variation is gradual.

The product is fed in at the intake 20 and moves downward by means of gravity alone in regulating duct 22 and measuring chamber 1 or measuring section 1', respectively. In regulating duct 22, movement of the product is retarded by the gate valve 31, so that the various product components c, d, and e to h come to lie upon one another in layers. Product component a is still located within the intake 20, and product component b is about to be divided into the two paths (regulating duct 22 and measuring section 1'). Product component i is leaving regulating duct 22 in the vicinity of gate valve 31. Even though the product is piled up to the height of the membrane 25, a high rate of flow results in regulating duct 22, corresponding to its throughput capacity and the cross section of the regulating duct. Circumstances are different in measuring section 1'. Here the downward movement of the product brought about by the force of gravity is retarded to a much greater extent by the shape of the measuring chamber 1, in particular, by the cross-sectional proportions in the electrical measurement area, that is, in the area of measuring section 1', and in the area of the constricted outlet aperture of measuring chamber 1. Consequently, product components e, f, g, h, i, and k are still located in measuring section 1', but no longer, in contrast, in regulating duct 22 laterally adjacent to measuring section 1'. The actual product content in measuring section 1' can have an order of magnitude from five liters up to twenty liters and more. In the area directly above the gate valve 31, equalization of rates occurs between the relatively large movement of the product emerging from regulating duct 22 and the comparatively small product movement out of measuring section 1'. In the case of measuring chamber 1 the lower aperture is decisive, which in addition may be preselected by means of a flap "K". From this description it may be seen that the rate of downward movement in measuring section 1' is several times smaller than the rate in regulating duct 22, roughly corresponding to the two product stream cross sections "A" and "B" if the upper cross sections of regulating duct 22 and measuring section 1' in the area of membrane 25 are approximately equal. The smaller the aperture "S" is adjusted by flap "K", the smaller the rate of downward movement of product in measuring section 1', the greater the period during which the product is held in measuring section 1', but the smaller the volume of each individual product component in measuring section 1', the greater the number of different product components in measuring section 1', and as a result, the more highly developed the product section formation.

Electrical measurement in accordance with FIG. 7 therefore encompasses a product section (average) of product components e to k. The effective measurement in this way lags somewhat behind the product stream, which offers another advantage, however, especially with the product section, since the addition of water than may be necessary—until it is effective in subsequent equipment—requires a certain amount of time. The aperture "S" and the overall throughout capacity of product through the gate valve 31 can be determined relative to each other such that either the greatest possible precision in the addition of water or optimal wetting of the product is achieved, and in this manner advantage may be taken of all the benefits of forward regulation (control) of the addition of moisture, which is preferably applied here.

The result of the foregoing descriptions is that the invention actually produces a substantial improvement in the measuring of moisture content and control of the required addition of water. The electrical measuring process, in particular, the capacitive measuring process, has the advantage that the entire content of the measuring section, for example, five to twenty liters, is measured continuously. The five to twenty liters cited, however, represents an average of 50, 100 or more liters of grain flowing through the measuring mechanism, due to the retardation of product described in measuring section 1'. This means that the moisture content measurement constantly misses grain on the order of magnitude of a sack and therefore offers representative results.

We claim:

1. Apparatus for continuously determining the moisture content of a product transported as a product stream, said product stream varying in moisture content along said stream, at least in part, passing through a measurement housing, said apparatus comprising means in said measurement housing for receiving said product stream and extracting a portion thereof, capacitive means in said measurement housing for continuously receiving said portion of said product stream, said capacitive means including a measuring section of a selected length wherein the moisture content of said portion is continuously measured as it passes through the measuring section and means controlling the relative flow rates of said portion within said capacitive means and the remainder of said product stream for accumulating enough of said portion along said measuring section length to permit determination of a pourable average of said product stream within said capacitive means.

2. A device in accordance with claim 1, further comprising product guide ducts in the measuring housing disposed substantially vertically.

3. A device in accordance with claim 1, wherein the device includes means for level regulating.

4. A device in accordance with claim 1, wherein the measurement housing includes a bypass duct associated with the measuring section to divert said remainder of the product, and regulating means for maintaining the product in the bypass at a constant level in order to product a predetermined backward accumulation of the product in measuring section, thereby providing a continuous averaging process.

5. A device in accordance with claim 4, wherein the measuring section and bypass duct are positioned directly adjacent to one another and are connected by a common product outlet and duct means for directing product overflow from the measuring section to the bypass.

6. A device in accordance with claim 5, wherein the measurement housing has a product inlet located essentially perpendicularly above the measuring section, and product is guided in free flow by the overflow duct means into the bypass.

7. A device in accordance with claim 6, further comprising throughput regulating means at the product outlet for retarding the product, and level sensor means for controlling said regulating means situated in the bypass duct.

8. A device in accordance with claim 7, wherein the level sensor comprising a membrane located at the side of bypass duct, and pneumatic actuating elements connect the membrane to the throughput regulating means.

9. A device in accordance with claim 7, further comprising a manual control means for opening and closing the throughput regulating means.

10. A device in accordance with one of claims 1, further comprising throughput measuring means for determining the instantaneous amount of product passing through the device.

11. A device in accordance with claim 1, further comprising a throughput regulating control loop having througput regulating means for retarding product movement, throughput measuring means for determining the instantaneous amount of product passing through the device and an electronic evaulator including a desired value control unit and means for comparing the actual value, supplied by throughput measuring means, to a desired value, supplied by said control unit, to control the throughput regulating means so as to maintain the desired value.

12. A device in accordance with claim 11, arranged directly beneath a storage container in such a manner that the output of the storage container is controlled by the device.

13. A device in accordance with claim 12, wherein the electronic evaluator includes a second computer means for controlling a subsequent device for wetting or drying.

14. A device in accordance with claim 1, wherein the capacitive device includes a weighing balance receptacle supported on a pressure pickup which provides a balance signal representative of product weight.

15. A device in accordance with patent claim 1, wherein the measurement housing has a measuring chamber, the measuring section being within the measuring chamber, the chamber having an outer wall, a vertical section of which serves as a first capacitor plate, a second capacitor plate being located inside the measuring chamber.

16. A device in accordance with claim 8, further comprising a manual control means for opening and closing the throughput regulating means.

17. A device in accordance with claim 2, further comprising a throughput regulating control loop having throughput regulating means for retarding product movement, throughput regulating means for retarding product movement, throughput measuring means for determining the instantaneous amount of product passing through the device and an electronic evaluator including a desired value control unit and means for comparing the actual value, supplied by throughput measuring means, to a desired value, supplied by said control unit, to control the throughput regulating means so as to maintain the desired value.

18. A device in accordance with patent claim 2, wherein the measurement housing has a measuring chamber, the measuring section being within the measuring chamber, the chamber having an outer wall, a vertical section of which serves as a first capacitor plate, a second capacitor plate being located inside the measuring chamber.

19. A device in accordance with claim 4, further comprising a throughput regulating control loop having throughput regulating means for retarding product movement, throughput measuring means for determining the instantaneous amount of product passing through the device and an electronic evaluator including a desired value control unit and means for comparing the actual value, supplied by throughput measuring means, to a desired value, supplied by said control unit, to control the throughput regulating means so as to maintain the desired value.

20. A device in accordance with patent claim 4, wherein the measurement housing has a measuring chamber, the measuring section being within the measuring chamber, the chamber having an outer wall, a vertical section of which serves as a first capacitor plate, a second capacitor plate being located inside the measuring chamber.

* * * * *